United States Patent [19]

Bjoernstijerna et al.

[11] Patent Number: 5,537,992

[45] Date of Patent: Jul. 23, 1996

[54] ANESTHETIC SYSTEM HAVING ELECTRONIC SAFETY INTERLOCK SYSTEM

[75] Inventors: Magnus Bjoernstijerna, Stockholm; Paer Emtell, Bromma; Georgios Psaros, Tullinge, all of Sweden

[73] Assignee: Siemens Elema AB, Solna, Sweden

[21] Appl. No.: 433,063

[22] Filed: May 3, 1995

[30] Foreign Application Priority Data

May 6, 1994 [SE] Sweden ................... 9401579

[51] Int. Cl.$^6$ .................. A61M 15/00; A61M 16/00
[52] U.S. Cl. .................. 128/203.14; 128/202.22; 128/200.19
[58] Field of Search .................. 128/202.22, 200.14, 128/200.19, 203.12, 203.14, 204.13, 204.14

[56] References Cited

U.S. PATENT DOCUMENTS

| | | | |
|---|---|---|---|
| 4,253,453 | 3/1981 | Hay | 128/200.19 |
| 4,307,718 | 12/1981 | Schreiber | 128/200.19 |
| 4,434,790 | 3/1984 | Olesen | 128/200.14 |
| 4,463,754 | 8/1984 | McDonald | 128/200.14 |
| 4,493,318 | 1/1985 | Mohr et al. | 128/200.19 |
| 4,759,358 | 7/1988 | Gregory | 128/200.14 |
| 4,867,212 | 9/1989 | Mohr et al. | 128/200.14 X |
| 4,883,049 | 11/1989 | McDonald | 128/202.22 |
| 4,982,734 | 1/1991 | Green et al. | 128/200.14 |
| 5,168,867 | 12/1992 | Falb et al. | 128/203.14 |
| 5,235,971 | 8/1993 | Falb et al. | 128/203.14 |
| 5,293,865 | 3/1994 | Altner et al. | 128/203.12 |

FOREIGN PATENT DOCUMENTS

| | | |
|---|---|---|
| 0376649 | 7/1990 | European Pat. Off. . |
| 2052271 | 1/1981 | United Kingdom . |
| 2060403 | 5/1981 | United Kingdom . |

OTHER PUBLICATIONS

Ohmeda BOC Health Care Brochure "The Tec 4 Range of Vaporizers", Sep. 1990.

*Primary Examiner*—Edgar S. Burr
*Assistant Examiner*—Eric P. Raciti
*Attorney, Agent, or Firm*—Hill, Steadman & Simpson

[57] ABSTRACT

A safety system is provided for anesthetic systems with at least two anesthetic vaporizers, the safety system preventing the simultaneous supply of anesthetic to a breathing circuit by more than one anesthetic vaporizer. The safety system which prevents this includes a setting means for each vaporizer which emits an activation signal when moved from an OFF position to an active position. The activation signal is received by a control unit which then sends a control signal to blocking valves, respectively arranged by the anesthetic vaporizers, and prevents the passage of breathing gas to more than one anesthetic vaporizer for vaporization of an anesthetic.

11 Claims, 2 Drawing Sheets

ANESTHETIC SYSTEM HAVING ELECTRONIC SAFETY INTERLOCK SYSTEM

BACKGROUND OF THE INVENTION

1. Field of the Invention

The present invention relates to a safety system for anesthetic systems of the type having at least two anesthetic vaporizers, each anesthetic vaporizer being equipped with a setting means which controls a vaporizer valve for setting a desired concentration of an anesthetic in the breathing circuit, the safety system preventing two or more anesthetic vaporizers from simultaneously supplying anesthetic to a breathing circuit in the anesthetic system.

2. Description of the Prior Art

In principle, narcosis, or anesthesia, means that a patient is rendered unconscious and unable to feel any pain. Usually, a mixture of oxygen ($O_2$), nitrous oxide ($N_2O$), anesthetic gas and possibly air is supplied to a patient via a breathing circuit in an anesthetic system. The most common anesthetic gases are halothane, desflurane, enflurane, isoflurane and sevoflurane. The anesthetic is normally in liquid form in an anesthetic vaporizer in the anesthetic system, and a desired amount of anesthetic gas is vaporized and delivered to the breathing circuit as anesthesia is induced in the patient. Since a muscle relaxant is also supplied in anesthesia, the patient is entirely dependent on the anesthetic system for maintenance of his or her breathing.

Different anesthetics have different effects on the patient. The side-effects of different anesthetics also differ. Anesthetic systems are thus available which can be equipped with plurality of anesthetic vaporizers so the anesthetist can choose the anesthetic he or she deems best for the patient without any need to connect or detach different anesthetic vaporizers. A mixture of different anesthetics, however, must not be supplied to the patient at the same time. The anesthetic system must therefore be devised so that only one anesthetic at time can be supplied to the patient.

For this purpose, it is known to provide vaporizers with an interlock system. One such system is described e.g. in the brochure "The Tec 4 Range of Vaporizers", Ohmeda, IN/028/9.90/E, September 1990. When one vaporizer is activated by turning setting knob, a cylindrical pin is mechanically extended from the sides of the vaporizer and locks, thereby preventing corresponding cylindrical pins on the surrounding vaporizer from being moved. The pins are mechanically connected to the setting knobs, thereby blocking the setting knobs on the other vaporizers.

Even if the locking of the other vaporizers would work satisfactorily in terms of patient safety, the mechanical interlock system has a number of disadvantages. For example, the setting knob must be turned a given distance before the mechanical locking is activated. Thus, the setting knob on many vaporizers could be in a position which deviates from the OFF position. As a result, it is not clear which vaporizer is, or is to be, activated. The interlock system's mechanical resistance also makes the setting knobs stiff, so a greater force becomes necessary for their activation.

Even with this type of mechanical interlock system, it is still possible for a mixture of different anesthetic gases to enter the breathing circuit. If one anesthetic vaporizer is turned off and another is immediately activated, two different anesthetic gases will mix in the breathing circuit and be supplied to the patient until complete gas exchange has occurred in the breathing circuit. Moreover, this known mechanical interlock system does not permit two anesthetic vaporizers containing the same anesthetic be connected and both activated in order to increase the concentration of this anesthetic in the breathing circuit, nor does it prevent simultaneous activation of two anesthetic vaporizers if one of the anesthetic vaporizers becomes defective and passes a flow of vaporized gas.

SUMMARY OF THE INVENTION

It is an object of the invention is to provide a safety system for anesthetic systems which permits the greatest possible safety and monitoring of anesthetic vaporization.

One such safety system is achieved in accordance with the invention wherein setting means are provided for each vaporizer (there being at least two vaporizers) for emitting an activation signal when changed from an OFF position to an active position, a control device is connected to the setting means to determine, on the basis of the activation signals, when any setting means has changed from its OFF position to its active position, and the control device thereupon generates a control signal capable of closing a blocking valve on each of the other anesthetic vaporizers, thereby preventing them from supplying anesthetic to the breathing circuit, even if one or more of the setting means of the other anesthetic vaporizers is/are activated.

An electronic interlock system of this kind achieves a safety system with a number of advantages compared to the known mechanical interlock system. The closed blocking valve prevents the activation of any other anesthetic vaporizers. The setting means are not restricted to setting knobs, but can be devised in a number of different ways. They can, for instance, be devised as keypads by which the anesthetist enters the desired concentration. The setting means can also consist of a lever or a knob, like the setting knobs used in the prior art. The safety system is accordingly not limited to the use of mechanical valves, and electronically controlled valves could alternatively be used. The availability of an activation signal can also be used for other purposes, e.g. to address and activate light-emitting diodes which clearly indicate which anesthetic vaporizer is supplying anesthetic gas to the breathing circuit. Irrespective of the way the setting means are actuated, the anesthetist can easily see which anesthetic gas is being supplied to the patient. The safety system can advantageously even be devised so that if one or more setting means on the other anesthetic vaporizers has been set to the active position, the blocking valves block vaporization of anesthetic in them, even if the first anesthetic vaporizer which was activated is shut off. This results in the requirement that all setting means must be set to the OFF position before another anesthetic vaporizer can be activated. This prevents the erroneous supply of more than one anesthetic gas to the breathing circuit.

The blocking valves can be valves which are separate from the vaporizer valves. This constitutes an additional safety feature for the anesthetic system, since no vaporization could then occur in the other anesthetic vaporizers, even if a vaporizer valve in one of them is defective. The blocking valve can also be devised as a control valve which serves as both a vaporizer valve and a blocking valve.

It is advantageous for the control device to be connected to an alarm unit, the control device then generating a second control signal if it determines, on the basis of activation signals from the setting means, that more than one setting means has been moved to the active position. The alarm unit emits an acoustic and/or visual alarm when the control device generates the second control signal.

Patient safety is then enhanced, since any attempt to activate a second anesthetic vaporizer, while a first anesthetic vaporizer is already activated, would result in an alarm, either an acoustic alarm or a visual alarm or a combination of the two. The anesthetist would then be made instantly aware of the situation and could take immediate action to remedy the fault. The visual alarm could be a blinking light-emitting diode or the like on the second anesthetic vaporizer.

One embodiment of the safety system is achieved in accordance with the invention wherein each setting means comprises setting knob, a position-indicating unit being arranged o the setting knob to indicate its position, and a position sensing unit arranged at the setting knob to sense the position-indicating unit, at least when the setting knob is in the OFF position. The position-sensing unit emits the activation signal which indicates whether the setting knob is in the OFF position.

A setting knob is the most common type of setting means used in anesthetic systems, and the ability to set it at a desired position with a simple twist of the wrist is an advantage. With a position-indicating unit on the setting means itself and a position-sensing unit by the setting knob, the position of the setting knob can be sensed, and the activation signal can be generated when the setting knob is turned from the OFF to the active position. There is no need for the position-sensing means to sense other setting knob positions, so the activation signal could therefore consist of a signal corresponding to a logical one or a signal corresponding to a logical zero (e.g. a break in an otherwise continuous signal).

Naturally, the reverse construction could also be used, i.e. with the position-indicating unit arranged at the setting knob and the position-sensing unit arranged on the setting knob.

The position-indicating unit can consist of a magnet and the position-sensing unit can consist of a magnetic field sensing component, preferably a Hall element. In practice, this will offer the simplest and most compact circuit for the position-sensing unit.

Alternatively, the position-indicating unit can be a coded marking on the setting knob, and the position-sensing unit could be a light-emitting component for directing light at the coded marking and a light-sensing component for detecting light reflected from the coded component.

In its simplest form, the OFF position, for example, could be designated with a high reflectivity surface, and the active position could be designated with a surface with poor reflectivity. More complex codes could also be used.

It is advantageous in connection with the embodiment using a coded marking if the coded marking consists of a bar code arranged on the setting knob across its entire setting range. The position-sensing unit can then read the position of the setting knob every time the knob is actuated, so that a defined target value for the concentration of the anesthetic in the breathing circuit is read by the control device. The control device regulates the vaporizer valve according to the target value thus read.

In this way, it is possible to provide the anesthetic system with complete electronic control and monitoring of the concentration of anesthetic gas in the breathing circuit. With anesthetic vaporizers using a mechanical vaporizer valve, control of the valve's accuracy becomes possible.

In another embodiment of the safety system for anesthetic systems in which the anesthetic vaporizers are detachably connected to the anesthetic system at connection sites designed for this purpose, a code element is arranged on each detachable anesthetic vaporizer and a code-sensing element is arranged at each connection site to sense the code element when an anesthetic vaporizer is connected. The code-sensing element is connected to the control device and sends a code signal to this device when an anesthetic vaporizer is connected.

With this improvement, it becomes possible to ensure that the intended anesthetic vaporizer is correctly attached to the anesthetic system.

In this context, it is advantageous for the code elements also to indicate which anesthetic is in the anesthetic vaporizer and for the control device, on the basis of the code signal from the code-sensing elements, to determine which anesthetics are connected to the anesthetic system.

Identification of the anesthetics makes it possible for the anesthetic system to supply extra heavy doses of anesthetic. In order to achieve this, the safety system for the anesthetic system can be devised with a switch arranged between the control device and each blocking valve, whereupon the control device determines, when two (or more) anesthetic vaporizers are activated, whether any two of them contain the same anesthetic, thereupon generating a switching signal which opens the switch between the control device and the blocking valves of the anesthetic vaporizers containing the same anesthetic to prevent the aforementioned control signal from reaching the blocking valves, so that the anesthetic vaporizers containing the same anesthetic can be activated at the same time.

As noted above, this option is not available in the mechanical interlock systems currently known for anesthetic systems. Especially at the start of anesthesia induction, supplying a large amount of anesthetic may be desirable so that the patient and the breathing circuit quickly are filled with the correct concentration of anesthetic.

In a further embodiment of the safety system in accordance with the invention, the control device contains means for storing information for a defined period of time after the shut-off of a first activated anesthetic vaporizer supplying anesthetic to the breathing circuit, indicating which anesthetic vaporizer was activated, and the control device emits regulatory signals if a second anesthetic vaporizer is activated within the defined period of time. The regulatory signals close the blocking valve connected to the second anesthetic vaporizer during a washout period and cause a washout valve to flush out gas containing the previously supplied anesthetic gas during the washout period, before anesthetic from the second activated anesthetic vaporizer is supplied to the breathing circuit.

This version of the safety system ensures that no mixture of different anesthetics is possible anywhere in the anesthetic system. In particular, the patient must not be exposed to a mixture of two anesthetics, which is a possibility with known interlock systems.

DESCRIPTION OF THE PREFERRED EMBODIMENTS

Figure 1:
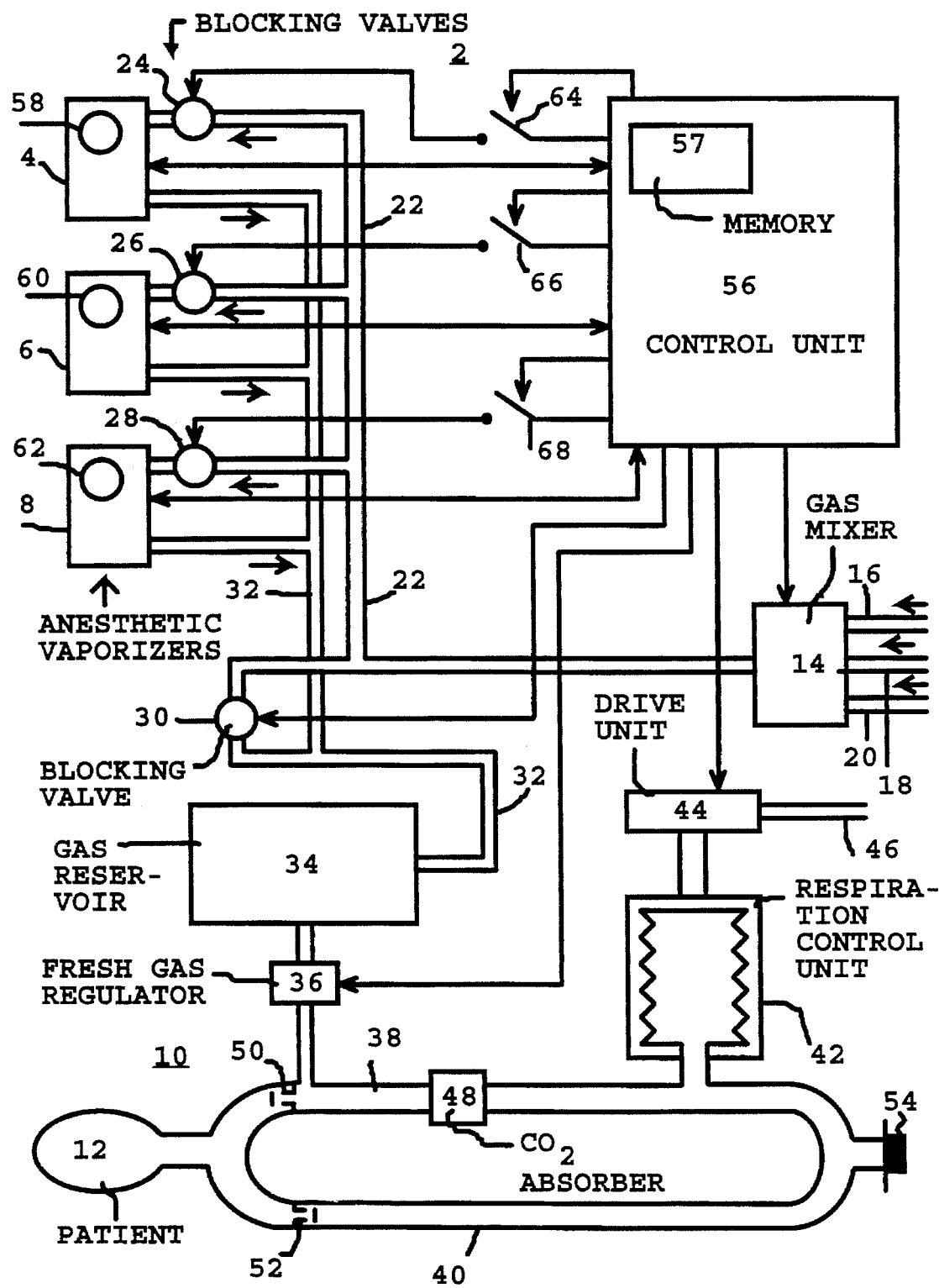
FIG. 1 is a schematic rendition of an anesthetic system with a safety system according to the invention.

FIG. 1 shows an anesthetic system 2 in which a first anesthetic vaporizer 4, a second anesthetic vaporizer 6 and a third anesthetic vaporizer 8 are connected for selectively supplying an anesthetic gas to a breathing circuit 10. The breathing circuit 10 then delivers a breathing gas containing the anesthetic gas to a patient 12.

Breathing gas is supplied in the anesthetic system 2 via a gas mixer 14. Gas can be delivered to the gas mixer 14 via a first gas connection 16, a second gas connection 18 and a third gas connection 20. The supplied gases can consist of air, nitrous oxide ($N_2O$) and oxygen ($O_2$). If only $O_2$ and $N_2O$ are to be supplied to the anesthetic system, the third gas connection 20 can either be closed or also used for supplying $O_2$. The supply of $O_2$ via two separate gas connections enhances patient safety. The inflowing gases are mixed in selectable proportions in the gas mixer 14 to form a breathing gas at a defined pressure, whereupon a defined flow of the mixed breathing gas is sent through a first gas line 22 toward the anesthetic vaporizers 4, 6 and 8. Each vaporizer 4, 6 and 8 has an input and an output, indicated by arrows showing the gas flow direction.

Near the input of the first anesthetic vaporizer 4 there is a first blocking valve 24, normally closed, which prevents gas from the first gas line 22 from passing through the first anesthetic vaporizer 4. In a corresponding manner, a second blocking valve 26 is arranged near the second anesthetic vaporizer 6, and a third blocking valve 28 is arranged near the third anesthetic vaporizer 8. When any of the anesthetic vaporizers 4, 6 or 8 is activated, the corresponding blocking valve 24, 26 or 28 is opened to pass a flow of gas from the gas mixer 14 through the activated anesthetic vaporizer 4, 6 or 8. To avoid more than one of the anesthetic vaporizers 4, 6 and 8 from simultaneously supplying anesthetics to the breathing system, the anesthetic circuit 2 has a safety system. This safety system will be described in greater detail below.

A fourth blocking valve 30 is arranged near the beginning of the first gas line 22, in which a flow of gas is conducted which has not passed through any of the anesthetic vaporizers 4, 6 or 8. The anesthetic system is devised so that the fourth blocking valve 30 automatically opens if all of the first blocking valve 24, the second blocking valve 26 and the third blocking valve 28 are closed. This ensures that the patient is supplied with breathing gas at all times.

When the fourth blocking valve 30 is open, breathing gas, with or without anesthetic gas, from the gas mixer 14 is sent through a second gas line 32 to a gas reservoir 34. The breathing gas is additionally mixed in the gas reservoir 34 to ensure that the vaporized anesthetic is mixed with the breathing gas as thoroughly as possible before gas is carried to the breathing circuit 10.

In the present embodiment, the breathing circuit 10 is a recirculating breathing circuit in which the patient rebreathes a larger or smaller amount of the gas in the breathing circuit 10. Here, the mixed gas in the gas reservoir 34 can appropriately be referred to as fresh gas for the breathing circuit 10. Fresh gas is sent to the breathing circuit 10 to compensate for the gas losses or gas discharges occurring in/from the breathing circuit 10, e.g. through intake of $O_2$ in the patient 12 and leakage in the circuit (including the patient 12). The supply of fresh gas to the breathing circuit 10 is regulated by a fresh gas regulator 36. The fresh gas is sent to an inspiratory line 38 in the breathing circuit 10 and is delivered thereby to the patient 12. From the patient 12, expired gas is carried in an expiratory line 40 to a respiration control unit 42. The respiration control unit 42 is, in the embodiment shown in FIG. 1, a bellows in a container. An inspiration can be imposed on the patient 12 when the bellows is compressed, and the patient is allowed to exhale when the bellows is released. Regulation of the respiration control unit 42 is performed by a drive unit 44 which, by means of compressed air from a fourth gas connection 46, can send a drive gas to the respiration control unit 42 and remove drive gas from this unit. A carbon dioxide absorber 48 is arranged in the inspiratory line 38 to remove carbon dioxide from the reused gas. A first check (one-way) valve 50 is also arranged in the inspiratory line 38 to control the direction of flow of breathing gas in the inspiratory line 38, and a second check valve 52 is arranged in the corresponding manner in the expiratory line 40 to regulate the direction of flow in the expiratory line 40. Surplus gas in the breathing circuit 10 is released by a pressure relief valve 54.

The anesthetic system 2 is controlled and monitored by a control unit 56. The control unit 56 regulates the operation of the gas mixer 14, the drive unit 44, the fresh gas regulator 36, the blocking valves 24, 26, 28 and 30 and the anesthetic vaporizers 4, 6 and 8. The control unit 56 also receives the settings made by the staff for e.g. breathing rate, desired tidal volume, the composition of the breathing gas etc. Other function and operations performed by the control unit 56 will be described below.

The first anesthetic vaporizer 4 is activated when a first setting knob 58 is turned, the second anesthetic vaporizer 6 is activated when a second setting knob 60 is turned and the third anesthetic vaporizer 8 is activated when a third setting knob 62 is turned. An activation signal is sent to the control device 56 when the anesthetist activates any of the setting knobs 58, 60 or 62. In its simplest form, the activation signal can consist of a zero signal, i.e. a break in the normal signal to the control unit 56.

Assume, for example, that the first anesthetic vaporizer 4 is to be activated, and that the anesthetist then turns the first setting knob 58 to a desired concentration of the selected anesthetic gas in the breathing circuit 10. The activation signal indicates to the control device 56 that the first blocking valve 24 is to he opened in order to pass a vaporized flow of breathing gas through the first anesthetic vaporizer 4. In the first anesthetic vaporizer 4 (as well as in the other anesthetic vaporizer), there is a vaporizer valve 73 which is mechanically connected to the first setting knob 58, thereby indicating the concentration of anesthetic which is to be achieved. The flow of breathing gas from the gas mixer 14 will then pass through the first gas line 22, through the first anesthetic vaporizer 4, in which the anesthetic is vaporized, and on through the second gas line 32 to the gas reservoir 34. From the gas reservoir 34, breathing gas and anesthetic gas then pass to the breathing circuit 10. Irrespective of the way in which the second setting knob 60 and the third setting knob 62 are actuated at this stage, the second blocking valve 26 and the third blocking valve 28 will remain closed. There is accordingly no vaporization of the anesthetic in the second anesthetic vaporizer 6 nor in the third anesthetic vaporizer 8.

For instances when a very large amount of anesthetic is required, e.g. at the start of induction of anesthesia in a patient, the safety system in the anesthetic system 2 is provided with a first switch 64 arranged between the control unit 56 and the first blocking valve 24, a second switch 66 arranged between the control unit 56 and the second blocking valve 26 and a third switch 68 arranged between the control unit 56 and the third blocking valve 28. All three switches 64, 66 and 68 are controlled by the control unit 56. An anesthetist could e.g. program the anesthetic system 2 in such a way that the control device 56, by opening one or more of the switches 64, 66 and 68, can prevent the corresponding one or ones blocking valves 24, 26 and 28 from closing. In this manner, two or three of the anesthetic vaporizers 4, 6 and 8 could be active at the same time. Here, it is assumed that the anesthetic vaporizers then contain the same anesthetic.

Figure 2:
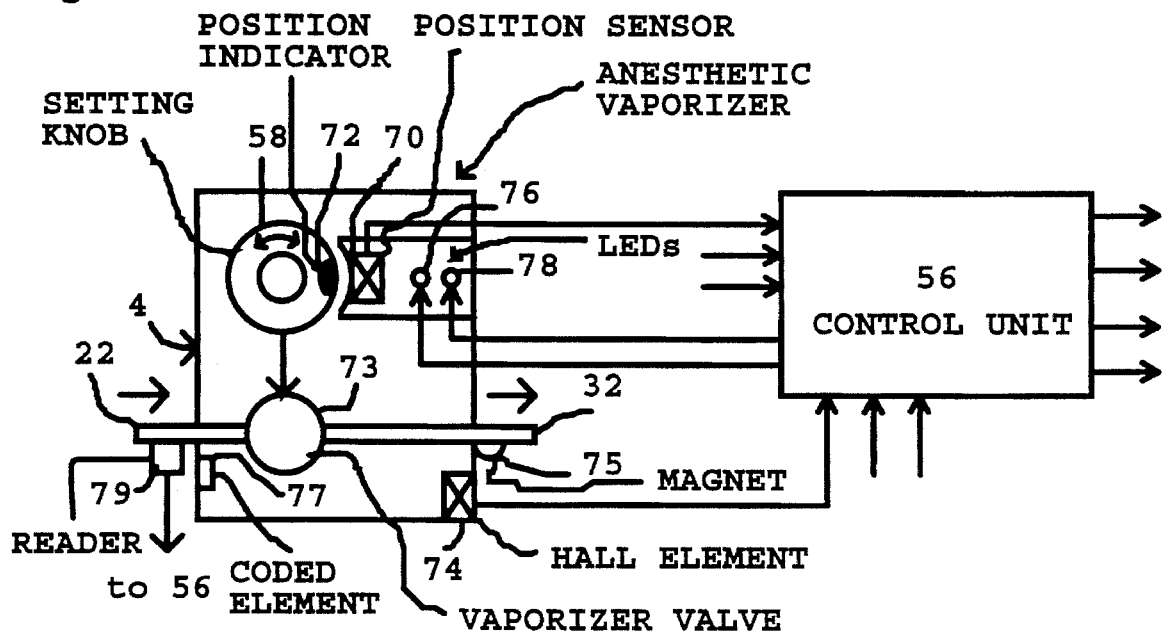
FIG. 2 shows an anesthetic vaporizer as used in the system of FIG. 1 and attendant safety system details.

Providing the anesthetic vaporizers with different identification markings for the different anesthetics will assist to increase safety so no incorrect programming can cause two or more different anesthetics to be supplied to the breathing circuit. An anesthetic can then be identified with a sensing unit by the control device 56 and only those switches 64, 66 or 68, which lead to blocking valves 24, 26 and 28 respectively connected to the anesthetic vaporizers 4, 6 and 8, will be permitted to open that are associated with vaporizers for the same anesthetic. This can be accomplished as shown in FIG. 2 by a coded element 77 being present on the input (or output) coupling to the vaporizer, the coded element 77 identifying the type of anesthetic supplied by the vaporizer. The coded element 77 is read by a code reader 79 disposed at the coupling location, which sends a signal to the control unit 56.

FIG. 2 shows in more detail the way in which the first anesthetic vaporizer 4 is constructed and the way in which signals are exchanged with the control unit 56. A position sensor 70, such as a Hall element, is mounted next to the setting knob 58. The position sensor 70 senses a position indicator 72, such as a magnet arranged on the first setting knob 58. As long as the setting knob 58 remains in the OFF position, the position sensor 70, if a Hall element, senses the process of the magnetic field and sends a signal to the control unit 56. This signal is arranged to correspond to a logical zero. When the first setting knob 58 is turned to activate the first anesthetic vaporizer 4, the position sensor 70 no longer senses the magnetic field, and an activation signal (corresponding to a logical one) is sent to the control device 56.

In order to ensure that the first anesthetic vaporizer 4 is correctly connected to the anesthetic system, a second Hall element 74 is disposed at a location at which the first anesthetic vaporizer 4 is connected to its gas input line or its gas output line. The input line or output line carries a magnet (such as magnet 75 shown for the output line in the example of FIG. 2) at its end which is coupled to the first anesthetic vaporizer 4. Instead of the use of a magnet 75 and a further Hall element 74, the aforementioned coded element 77 and code reader 79 can be used for this purpose as well. If the first anesthetic vaporizer 4 is not correctly connected, a signal corresponding to a logical one is generated and sent to the control unit 56. When the first anesthetic vaporizer 4 is correctly connected to the anesthetic system 2, a signal corresponding to a logical zero is generated and sent to the control unit 56.

A first light-emitting diode 76 and a second light-emitting diode 78 are also arranged on the first anesthetic vaporizer 4. The first light-emitting diode 76 emits a green signal if the first anesthetic vaporizer 4 is activated in order to show that the first anesthetic vaporizer 4 is active and supplying an anesthetic to the breathing gas in the breathing circuit 10. If one of the other anesthetic vaporizers 6 or 8 is already activated at the time the first anesthetic vaporizer 4 is activated, the second light-emitting diode 78 would instead serve as an alarm and blink to indicate that another anesthetic vaporizer 6 or 8 had already been activated. In addition, the first blocking valve 24 would remain closed. The two light-emitting diodes 76 or 78 preferably have different colors in order to further ensure that the alarm is noticed. In addition, an acoustic alarm can be connected to ensure that the anesthetic system makes the operator aware that an attempt has been made to activate a second anesthetic vaporizer.

The second anesthetic vaporizer 6 and the third anesthetic vaporizer 8 are equipped in a corresponding manner and are connected to the control unit 56. This is indicated in FIG. 2 with a number of incoming and outgoing signal lines to/from the control unit 56.

Figure 3:
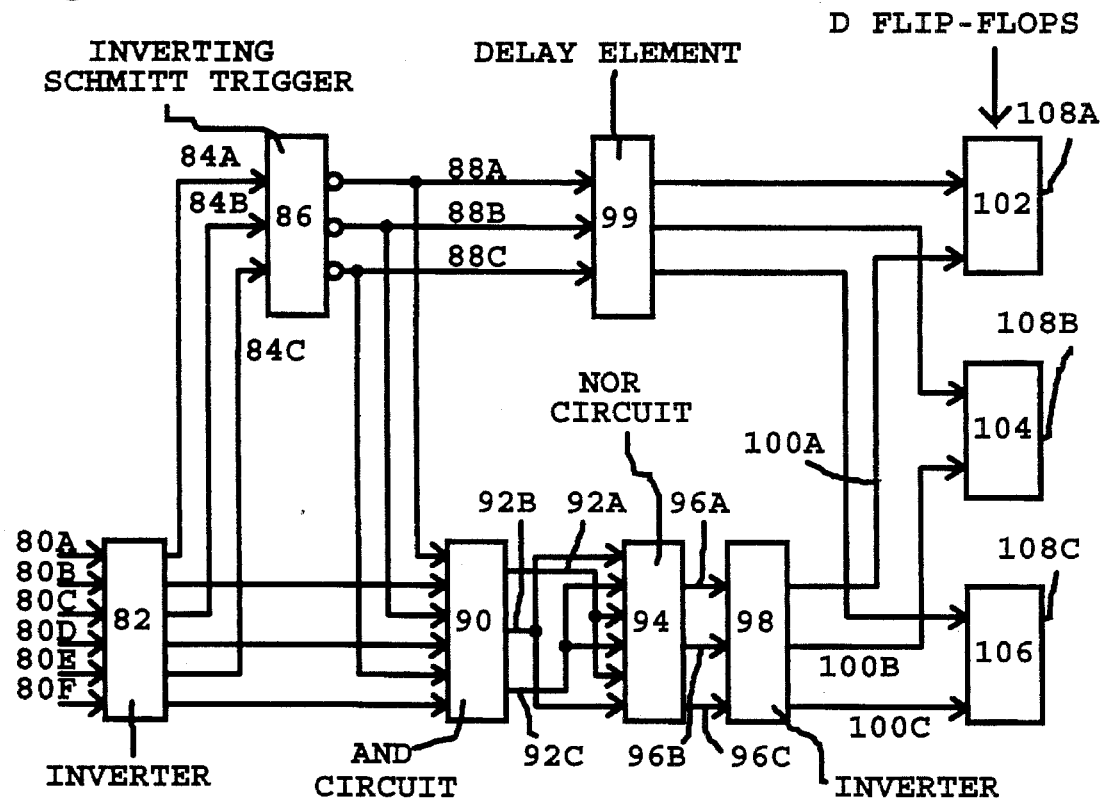
FIG. 3 shows an embodiment of an electronic circuit for preventing more than one anesthetic vaporizer of the type shown in FIG. 2 from being activated at the same time.

One possible way to achieve blocking of the anesthetic vaporizers 4, 6 and 8 which are not to be activatable is shown in the circuit diagram in FIG. 3. The signal from the first Hall element 70 is designated as the input signal 80A, and the signal from the second Hall element 74 is designated as the input signal 80B. In the corresponding way, the input signals 80C, 80D, 80E and 80F are respective signals from the Hall element of the second anesthetic vaporizer 6 and the Hall element of the third anesthetic vaporizer 8. With three correctly connected anesthetic vaporizers 4, 6 and 8, each in its OFF-position, the sequence of input signals to the control unit 56 will be 000000. Each signal is individually inverted in a first inverter 82, and the output signals from the first inverter 82 are designated 84A, 84B, 84C, 84D, 84E, 84F (signal sequence: 111111). The three inverted signals respectively corresponding to the signal at one setting knob 84A, 84C or 84E are sent to an inverting Schmitt trigger 86. The output signals from the inverting Schmitt trigger 86 are designated 88A, 88B, 88C (signal sequence: 000). The three inverted signals which indicate whether the anesthetic vaporizers are correctly connected (84B, 84D, 84F) are sent to an AND circuit 90 and compared there in pairs with the respective output signal 88A, 88B, 88C from the inverting Schmitt trigger 86, i.e. the signals 88A and 84B are sent to a first AND element in the AND circuit 90, the output signal from this element being designated 92A, the signals 88B and 84D are sent to a second AND element in the AND circuit 90, the output signal being designated 92B, and the signals 88C and 84F are sent to a third AND element in the AND circuit 90, generating an output signal designated 92C. As long as the anesthetic vaporizers are correctly installed and OFF, the output signals from the AND circuit 92A, 92B and 92C will be logical zeros (signal sequence: 000). The output signals 92A, 92B, 92C from the AND circuit 90 are sent cross-wise to a NOR circuit 94 to be compared in pairs. Thus the signals 92B and 92 are sent to a first NOR element in the NOR circuit 94 an generate an output signal 96A, the signals 92A and 92C are sent to a second NOR element in the NOR circuit 94 and generate an output signal 96B and the signals 92A and 92B are sent to a third NOR element in the NOR circuit 94 and generate a output signal 96C. With only logical zeroes as the input signal, the output signals 96A, 96B and 96C will be logical ones (signal sequence: 111). These signals are sent to a second inverter 98 which supplies the output signals 100A, 100B and 100C (signal sequence: 000). The output signal 100A is sent to the input terminal on a first D flip-flop 102, the output signal 100B is sent to the input terminal on a second D flip-flop 104 and the third output signal 100C is sent to the input terminal on a third D flip-flop 106. The first D flip-flop 102 is clocked with the output signal 88A from the inverting Schmitt trigger 86, the second D flip-flop 104 is clocked with the output signal 88B from the inverting Schmitt trigger 86 and the third D flip-flop 106 is clocked with the output signal 88C from the inverting Schmitt trigger 86. In order to ensure that the output signals 100A, 100B and 100C to the respective D flip-flop 102, 104 and 106 have time to change before the clocking signal arrives, a delay element 99 is incorporated between the inverting Schmitt trigger and the D flip-flops 102, 104 and 106. The delay element 99 delays clocking of the D flip-flops 102, 104 and 106 by an appropriate interval. The output signal 108A from the first D flip-flop 102 is sent to the first blocking valve 24, the output signal 108B from the second D flip-flop 104 is sent to the second blocking valve 26 and the output signal 108C from the third D flip-flop 106 is sent to the third blocking valve 28. When the anesthetic system starts, the output signals 108A, 108B and 108C are logical zeroes, and the blocking valves 24, 26 and 28 are closed.

It is now assumed that the first anesthetic vaporizer 4 is activated by turning the first setting knob 58. An activation signal is then generated when the Hall element 70 senses that the magnet 72 is moved. In other words, the input signal 80A, changes from a logical zero to a one (input signal sequence: 100000). As a result of inversion in the first inverter 82, the output signal 84 is therefore a logical zero (signal sequence: 011111). Here, the inverting Schmitt trigger 8 will generate a clock signal (a logical one) as the output signal 88A (signal sequence: 100), activating the first flip-flop 102 after the delay in the delay device 99. The input signal 100A to the first D flip-flop 102 is a logical one, so the first D flip-flop 102 produces a logical one as the output signal 108A, thereby causing the first blocking valve 24 to open. In the AND circuit 90 (input signal sequence: 110101), even the output signal 92A will accordingly switch to a logical one. As a result, the output signals 96B and 96C from the NOR circuit 94 become logical ones (signal sequence:011). In the second inverter 98, these ones are inverted into logical zeroes, so the signals 100B and 100C, which serve as input signals to the second D flip-flop 104 and the third D flip-flop 106 respectively, become logical zeroes (signal sequence: 100). But since the input signals 88B and 88C to the second and third D flip-flop 104 and 106 respectively are logical zeroes, output signals from them are not affected. The second and third blocking valve 26 and 28 remain closed.

It is now assumed further that the third anesthetic vaporizer 8 is also activated. This means that the input signal 80E will be a logical one (input signal sequence: 100010) which is the inverted in the first inverter 82, so the input signal 84E t 35 the inverting Schmitt trigger 86 will be a logical zero signal sequence: 010). The output signal 88C from the inverting Schmitt trigger 86 will then be a logical one which activates the third D flip-flop 106 (signal sequence: 101). Since, the input signal 100C to the third D flip-flop 106 is a logical zero, however, the output signal 108C therefore remains a logical zero and the third blocking valve 28 remains closed. Thus no vaporization is possible in the third anesthetic vaporizer 8. In the rest of the circuit, the output signal 96 from the NOR circuit will also be a logical one (signal sequence: 111), and the input signal 100A to the first D flip-flop 102 will accordingly be a logical zero as well. Since the first D flip-flop 102 cannot be clocked until the first setting knob 58 is turned to the OFF position and then reactivated, the output signal 108A remains a logical one, and the first blocking valve 24 remains open.

The circuit diagram shown in FIG. 3 can be devised in other ways and can be augmented with other safety function ensuring that only one blocking valve at a time can be open (except when one or more of the switches 64, 66, 68 is/are open). This function can also be implemented as firmware in a microprocessor.

Instead of a Hall element and a magnet on the setting knob, position indicator 72 on the setting knob can be some kind of coded pattern marking, which is illuminated with a light-emitting diode, and a photodiode which senses the pattern of reflected light and, accordingly, also senses when the setting knob is turned, the light-emitting diode and the photodiode forming the position sensor 70. In its simplest version, the OFF position can be marked with a low-reflectivity surface, and the active position can be marked with a high-reflectivity surface. In a more advanced form, the pattern can consist of e.g. a Gray code which also indicates the concentration set. Anesthetic systems normally have a concentration meter in the breathing circuit for measuring the concentration of anesthetic. When the desired concentration is read and the true concentration is measured, the control unit, if equipped with additional alarm functions, can indicate whether the concentration is too low or too high.

Another option provided by the described safety system is minimization of the possibility of two anesthetics being mixed in the breathing circuit 10. Anesthetists sometime wish to switch anesthetics during an operation. Such a switch 5 could result in the mixing of two anesthetics in the breathing circuit 10. The control unit 56 can therefore be appropriately equipped with a memory 57 which stores information identifying which anesthetic vaporizer is activated. If the active anesthetic vaporizer is then turned off and another anesthetic vaporizer is activated within a defined period of time, the fourth blocking valve 30 would first be activated so breathing gas, without anesthetic, passes into the gas reservoir 34 and the breathing circuit 10 in order to flush out the first anesthetic. Only after this occurs does the blocking valve open to permit the activated anesthetic vaporizer to supply new anesthetic to the breathing circuit 10.

There is no need for a mechanical vaporizer valve connected to the setting knob. An electronically controlled valve for regulating vaporization of the anesthetic in the anesthetic vaporizers is also conceivable. The setting knob could then be replaced by some other form of setting means, e.g. a keypad, with which the desired concentration can be entered or some kind of knob for actuating a potentiometer or the like. In these instances, the vaporizer valve and the blocking valve could be of a single common valve.

Although modifications and changes may be suggested by those skilled in the art, it is the intention of the inventors to embody within the patent warranted hereon all changes and modifications as reasonably and properly come within the scope of their contribution to the art.

We claim as our invention:

1. An anesthetic system comprising:

a breathing circuit having a connection adaptable for respiratory connection to a patient;

a source of input gas;

at least two gas flow paths between said breathing circuit and said source of input gas, said at least two gas flow paths being partially united;

at least two anesthetic vaporizers respectively disposed in the at least two gas flow paths, each anesthetic vaporizer having an input connected for receiving gas from said source of input gas via said respective gas flow path, and an output connected via said gas flow path for supplying gas containing an anesthetic to said breathing circuit, and a vaporizing valve disposed between said input and said output, and each anesthetic vaporizer having setting means for controlling said vaporizer valve to supply a selected concentration of said anesthetic in said gas to said output;

at least two blocking valves respectively disposed in the at least two gas flow paths;

each setting means having an OFF position, at which all setting means are initially set, at which no anesthetic from the anesthetic vaporizer enters into the gas in the gas flow path for that anesthetic vaporizer, and each setting means having an active position, to which each setting means can be individually changed from its OFF position, at which said selected concentration of anesthetic from that anesthetic vaporizer enters into the gas in the gas flow path; and a safety system including signal emitter means, in each anesthetic vaporizer, for emitting an activation signal when the setting means in that anesthetic vaporizer is changed from its OFF position to its active position, and control means, supplied with the activation signal, for identifying the anesthetic vaporizer whose setting means is in the active position and for supplying a control signal to the blocking valve for each of a remainder of said anesthetic vaporizers, other than the identified anesthetic vaporizer, for closing said blocking valves and preventing each anesthetic vaporizer in said remainder of anesthetic vaporizers from supplying any anesthetic to said breathing circuit regardless of any subsequent change in the position of the respective setting means of the anesthetic vaporizers in said remainder of anesthetic vaporizers.

2. An anesthetic system as claimed in claim 1 wherein each anesthetic vaporizer comprises a single control valve means for operating both as said vaporizer valve and said blocking valve.

3. An anesthetic system as claimed in claim 1 wherein said control means comprises means for generating an alarm signal if said control device receives more than one activation signal, and means for generating a humanly perceptible alarm in response to said alarm signal.

4. An anesthetic system as claimed in claim 1 wherein each anesthetic vaporizer includes means for detachably connecting said anesthetic vaporizer to said source of input gas and to said breathing circuit at coupling sites, and each anesthetic vaporizer comprising a coupling indicator at one of said coupling sites, and detector means for detecting the presence of said coupling indicator and for generating a signal supplied to said control unit indicating that the anesthetic vaporizer is connected to said breathing circuit.

5. An anesthetic system as claimed in claim 1 further comprising a washout valve, controllable by said control means, connected between all of said anesthetic vaporizers and said breathing circuit, and wherein said control means comprises memory means for, when the setting means of an anesthetic vaporizer supplying anesthetic to said breathing circuit is returned to the OFF position, storing an identification of that anesthetic vaporizer as a last-activated anesthetic vaporizer, and said control unit comprising means, if a different one of said anesthetic vaporizers is activated within a predetermined period of time following deactivation of said last-activated anesthetic vaporizer, generating a signal for closing the blocking valve associated with said different anesthetic vaporizer during a washout phase and for simultaneously closing said washout valve for flushing out any remaining gas from said last-activated anesthetic vaporizer before anesthetic from said different anesthetic vaporizer is supplied to said breathing circuit.

6. An anesthetic system as claimed in claim 1 wherein each anesthetic vaporizer is connected to said source of input gas and to said breathing circuit at respective coupling sites, and each anesthetic vaporizer comprising a coded element at one of said coupling sites identifying a type of anesthetic supplied to said breathing circuit by that anesthetic vaporizer, and reader means for reading said coded element and for supplying a signal to said control means for identifying said type of anesthetic.

7. An anesthetic system as claimed in claim 6 comprising at least three of said anesthetic vaporizers, two of said anesthetic vaporizers containing the same anesthetic, and further comprising a switch disposed between said control means and each of said blocking valves, and wherein said control means comprises means for determining, on the basis of said signals identifying the type of anesthetic in each anesthetic vaporizer connected to said breathing circuit and when the respective setting means of two or more of said anesthetic vaporizers are in an activated position, whether any of said two or more anesthetic vaporizers contains the same anesthetic and for generating a switching signal for opening the switch at each of said anesthetic vaporizers containing the same anesthetic for preventing a signal from being supplied to the respective blocking valves for those anesthetic vaporizers containing the same anesthetic so that said anesthetic vaporizers containing the same anesthetic can simultaneously supply anesthetic to said breathing circuit.

8. An anesthetic system as claimed in claim 1 wherein said setting means comprises a setting knob carrying a position-indicating element, and wherein said signal emitting means comprises means for sensing a position of said position-indicating element for sensing when said setting knob is in said OFF position and for emitting said activation signal when said setting knob is not in said OFF position.

9. An anesthetic system as claimed in claim 8 wherein said position indicating element comprises a magnet, and wherein said signal emitting element comprises a Hall element.

10. An anesthetic system as claimed in claim 8 wherein said position indicating element comprises a coded marking on said setting knob, and wherein said signal emitting means comprises a light-emitting element disposed to emit light at said coded marking and a light-sensing element for detecting light reflected from said coded marking.

11. An anesthetic system as claimed in claim 10 wherein said coded marking comprises a bar code disposed on said setting knob along an entire setting range of said setting knob, and wherein said signal emitting means comprises means for reading a position of said setting knob every time said setting knob is actuated, wherein said control means comprises means for storing a defined target value for said concentration of anesthetic from that anesthetic vaporizer, and said control means including means for regulating said vaporizer valve dependent on said target value and the position of the setting knob read by said means for reading.

* * * * *